US011058574B2

(12) United States Patent
Michels et al.

(10) Patent No.: US 11,058,574 B2
(45) Date of Patent: Jul. 13, 2021

(54) INTRAOCULAR INJECTION SYSTEM AND METHODS FOR CONTROLLING SUCH A SYSTEM

(71) Applicant: OPHTHOROBOTICS AG, Klosers (CH)

(72) Inventors: Stephan Michels, Klosters (CH);
Matthias Becker, Klosters (CH);
Bradley Nelson, Klosters (CH);
Franziska Ullrich, Klosters (CH)

(73) Assignee: OPHTHOROBOTICS AG, Klosters (CH)

( * ) Notice: Subject to any disclaimer, the term of this patent is extended or adjusted under 35 U.S.C. 154(b) by 290 days.

(21) Appl. No.: 15/741,459

(22) PCT Filed: Jul. 3, 2015

(86) PCT No.: PCT/EP2015/065209
§ 371 (c)(1),
(2) Date: Jan. 2, 2018

(87) PCT Pub. No.: WO2017/005277
PCT Pub. Date: Jan. 12, 2017

(65) Prior Publication Data
US 2018/0360654 A1 Dec. 20, 2018

(51) Int. Cl.
*A61F 9/00* (2006.01)
*A61B 34/30* (2016.01)
(Continued)

(52) U.S. Cl.
CPC ............ *A61F 9/0008* (2013.01); *A61B 34/30* (2016.02); *A61M 5/3287* (2013.01);
(Continued)

(58) Field of Classification Search
CPC ...... A61M 5/158; A61M 5/32; A61M 5/3287; A61M 2005/1585; A61M 2005/1588;
(Continued)

(56) References Cited

U.S. PATENT DOCUMENTS 4,713,060 A 12/1987 Riuli
6,079,449 A 6/2000 Gerber
(Continued)

FOREIGN PATENT DOCUMENTS

CN 204133966 U 2/2015
CN 104540447 A 4/2015
(Continued)

*Primary Examiner* — Bhisma Mehta
*Assistant Examiner* — James D Ponton
(74) *Attorney, Agent, or Firm* — Christensen, Fonder, Dardi & Herbert PLLC (57) ABSTRACT

An intraocular injection system for injecting a substance into an eye globe of an animal or human eye, the system comprising an injection device with a piercing member for injection of the substance into the eye globe, the intraocular injection system providing an automated piercing of the eye globe by the piercing member. The system further comprises a robotic manipulator carrying the injection device, the robotic manipulator adapted and configured to move the injection device to a pre-injection position, a detection device adapted and configured to detect a position of a patch placed onto the eye globe and to control the robotic manipulator to move the injection device to the pre-injection position, the pre-injection position being based upon the detected position of the patch on the eye globe.

25 Claims, 7 Drawing Sheets

(51) Int. Cl.
    *A61M 5/32*     (2006.01)
    *A61B 17/34*     (2006.01)
    *A61B 90/00*     (2016.01)
    *A61B 90/40*     (2016.01)

(52) U.S. Cl.
    CPC . *A61B 2017/3409* (2013.01); *A61B 2090/064* (2016.02); *A61B 2090/401* (2016.02); *A61M 2210/0612* (2013.01)

(58) Field of Classification Search
    CPC .......... A61M 2210/0612; A61F 9/0008; A61F 9/0026; A61F 9/007; A61F 9/00736; A61F 9/00754; A61F 9/0017; A61B 2017/3405; A61B 2017/3409; A61B 34/30; A61B 34/70; A61B 2090/401; A61B 90/50
    See application file for complete search history.

(56) References Cited

U.S. PATENT DOCUMENTS

| | | | |
|---|---|---|---|
| 6,264,665 B1 * | 7/2001 | Yu | A61B 90/10 606/130 |
| 7,100,646 B2 * | 9/2006 | Py | A61J 1/1406 141/329 |
| 7,146,983 B1 * | 12/2006 | Hohla | A61F 9/00806 128/898 |
| 8,287,494 B2 * | 10/2012 | Ma | A61F 9/0017 604/151 |
| 8,509,503 B2 | 8/2013 | Nahum et al. | |
| 2009/0216067 A1 | 8/2009 | Lebosse et al. | |
| 2011/0125165 A1 * | 5/2011 | Simaan | A61B 34/72 606/130 |
| 2012/0265149 A1 * | 10/2012 | Lerner | A61M 5/3243 604/190 |
| 2013/0289581 A1 * | 10/2013 | Yeung | A61B 17/00 606/130 |
| 2014/0012226 A1 | 1/2014 | Hochman | |
| 2014/0018663 A1 | 1/2014 | Harmer et al. | |

FOREIGN PATENT DOCUMENTS

| | | |
|---|---|---|
| JP | S62-299270 A | 12/1987 |
| JP | H05-53611 U | 7/1993 |
| JP | 2000-508209 A | 7/2000 |
| JP | 2003-511206 A | 3/2003 |
| JP | 2009-540999 A | 11/2009 |
| JP | 2010-530268 A | 9/2010 |
| JP | 2011-200618 A | 10/2011 |
| WO | WO 97/38652 A1 | 10/1997 |
| WO | WO 01/28476 A1 | 4/2001 |
| WO | WO 2009/140688 A2 | 11/2009 |
| WO | WO 2011/088400 A2 | 7/2011 |
| WO | WO 2012/018823 A2 | 2/2012 |

* cited by examiner

INTRAOCULAR INJECTION SYSTEM AND METHODS FOR CONTROLLING SUCH A SYSTEM

RELATED APPLICATIONS

The present application is a National Phase entry of PCT Application No. PCT/EP2015/065209, filed Jul. 3, 2015, the disclosure of which is hereby incorporated by reference herein in its entirety.

FIELD OF THE INVENTION

The invention relates to an intraocular injection system and methods for controlling such a system.

BACKGROUND OF THE INVENTION

Intraocular injections have to be made precisely in order to avoid damage to parts of the eye. Usually, medical doctors perform such injections by inserting a needle attached to a syringe filled with a substance, for example, a drug, into a suitable location and to a suitable depth of the patient's eye, injecting the drug into the eye and withdrawing the needle from the eye. However, before performing the injection, due care must be given to pre-injection preparation steps. Important pre-injection steps comprise placing a speculum to the eye lids, disinfecting the eye and administering anesthesia to the eye. Usually, prior to an injection into an eye globe, there is a need to sufficiently rinse the accessible portions of the eye globe by a disinfectant such as povidone-iodine. Due to the high level of microbial activity, in particular in the area of the eyelid, the step of disinfecting the accessible portions of the eye globe cannot guarantee success. This is because iodine concentration and exposure time may not be increased indefinitely due to discomforting side effects for the patients. Therefore, with regards to a sterile injection scenario, there is a first trade-off to be made.

Furthermore, after having prepared the eye globe for the injection, while holding the syringe, the medical doctor has to remove a cover exposing the sterile piercing member (needle) to the environment. For an experienced medical doctor the time between the removal of the cover and the injection may only take several seconds. However, this is enough time to incur a risk of microbial contamination of the needle by a dust particle and/or a droplet. Investigations have been carried out on eye inflammations that occurred after intraocular injections. Such investigations indicate that in particular in environments where medical doctors did not, or did not always, wear surgical face masks, and when the injections were not performed under operating theater conditions, the risk of inflammation was significantly higher as compared to other environments and conditions. The majority of inflammations could be connected to oral microbial activity of the respective medical staff.

Apart from manual injection systems, some automated injection systems are known from prior art documents. For example, U.S. Pat. No. 8,287,494B2 describes an intraocular injection system that automatically translates the needle into the eye, dispenses the drug to be injected and retracts the needle from the eye. Therefore, this simple intraocular injection system comprises an injection device with a piercing member for injection of a substance into the eye globe, wherein the intraocular injection system provides an automated piercing of the eye globe by the piercing member. This is achieved by a mechanical movement performed by the system and triggered by a medical doctor.

The medical doctor has to manually position and actuate this automated system. Therefore, all of the above-described trade-offs and risks with regards to contamination exist as well.

SUMMARY OF THE INVENTION

It is an objective of this invention to provide an intraocular injection system and methods for controlling such a system that provide substantially less risk of performing intraocular injections that incur inflammation after injection.

This problem is solved by intraocular injection systems and methods described herein, including the system of claim 1 and the method of claim 22.

According to the invention, the intraocular injection system comprises:

a robotic manipulator carrying the injection device, the robotic manipulator adapted and configured to move the injection device to a pre-injection position, a detection device adapted and configured to detect a position of a patch placed onto the eye globe and to control the robotic manipulator to move the injection device to the pre-injection position, the pre-injection position being based upon the detected position of the patch on the eye globe.

The intraocular injection system is configured to detect a position of a patch that has been placed beforehand onto the eye globe, and in particular on the conjunctiva of the eye globe covering a predetermined injection point. On the basis of the detected position, the robotic arm is controlled to move the injection device into a pre-injection position. The pre-injection position has a close spatial relationship between patch and the tip of the piercing member of the injection device. Usually, the pre-injection position of the piercing member is situated above the patch. Preferably the tip of the piercing member is at a distance to the patch of 10 mm to 80 mm, more preferably at 20 mm to 60 mm and even more preferably at 30 mm to 50 mm. This is because starting from the pre-injection position a penetration action into the eye globe is performed by an automated movement of the piercing member piercing through the patch and the underlying conjunctiva and sclera.

Preferably, such a patch comprises a polymer and/or is a hydrogel and has disinfectant and/or anesthetic properties. Usually, the patch has a diameter of several millimeters, preferably at least three millimeters and less than eight millimeters. It may have various shapes like circular, oval or ring shaped. The thickness of the patch on the eye globe ranges from at least half a millimeter to several millimeters depending on the material and its properties. In particular shape and thickness of the patch allow a reliable recognition by the detection device. If adjusted properly, there is no need for the pre-injection preparation steps like disinfecting the eye globe and/or administering anesthesia to the eye globe. According to a method of the present invention, there is no need to rinse the accessible parts of the eye globe by a disinfectant. When the patch has a disinfectant property, it is sufficient to attach the patch covering the previously located injection spot on the eye globe's conjunctiva. After a sufficient amount of time for disinfecting at least in the area directly covered by the patch, the penetration of the eye globe is performed by piercing through the patch into the eye globe. Preferably, the penetration is done to perform an injection of a substance into the eye globe. However, as an alternative or in combination it is as well possible to extract tissue and/or liquid from the inside of the eye globe via the piercing member or to place and use other instruments inside the eye globe if the piercing member is a trocar.

Furthermore, the injection device is adapted and configured to automatically perform the injection starting from the pre-injection position if triggered by a medical doctor. The physical presence of a human such as a medical doctor is not needed at the patient's site to perform the injection. Rather, the system can be remotely steered, monitored and/or triggered. Thus, the presence of microbial contamination sources may be reduced or avoided before, during or after the injection.

According to the present invention, intraocular injections comprise in particular intravitreal injections. However, according to the illnesses to be treated and substances to be delivered, other intraocular injections are certainly comprised as well. The delivered substances may contain drugs and/or viral vectors.

Preferably, the injection device is a mechanical injection device comprising a syringe connected to a needle serving as the piercing member. The syringe can be a common single-use syringe made for manual intraocular injections comprising a plunger which fits tightly in a cylindrical tube. Alternatively, the injection device comprises a syringe body having a cylindrical tube fitted with a membrane and having two valves, one of which is adapted and configured for pulling a liquid substance such as a drug or a cleaning solution or a disinfectant, into the syringe body, and the other one being adapted and configured for pushing out a liquid in the syringe body. According to this embodiment it is preferable to use exchangeable single-use needles as a part of the injection device.

Preferably, the injection device comprises a control unit for triggering the start of the injection movement of the piercing member. The control unit can be adapted to receive a signal from a medical doctor being present near the patient or being remote. The injection device is preferably adapted to automatically perform the intraocular injection process by mechanical translation of the piercing member penetrating through the patch and conjunctiva into the eye globe, delivering the substance and retracting the piercing member from the eye globe, the piercing member then returning to the pre-injection position or even moving beyond this position away from the eye globe. Preferably, a medical doctor is authorizing and triggering the injection process after having verified the identity of the patient, the position of the patch, the pre-injection position of the injection device, and the necessary resting time of the patch to provide sufficient disinfection. All of this may be performed remotely using cameras and/or sensors of the detection device and other means of the system. Preferably, the injection device comprises a suitable electronic motor combined with a spindle drive.

In a preferred embodiment the detection device is adapted and configured to detect a difference between a topology of the eye globe without the patch and a resultant topology of the combined eye globe and patch. Detecting the topology of the eye globe with and without the patch can be achieved for example by a camera-sensor combination using structured light or a time-of-flight distance sensor or phase shift sensors. Optical resolution of the detection device's cameras and/or sensors is decisive in order to detect the patch. Therefore, a combination of several cameras and/or sensors may be necessary. As an alternative, or in addition to the topology change, appropriate sensors detect optical properties of the eye globe combined with the patch. For example, a change of the infrared surface picture caused by the patch and/or a fluorescence wavelength signal emitted by the patch or parts of the patch and triggered by illuminating the patch with wavelengths shorter than the fluorescent wavelength.

Preferably, the system further comprises an airflow device providing a flow of sterile air enveloping the piercing member of the injection device. To preserve the sterile nature of an intraocular injection, the piercing member, such as a needle that must be exposed from its cover shortly before the injection, must not come into contact with microbial matter via the air before it translates into the eye globe. Therefore, such a flow of sterile air enveloping the piercing member is a preferred solution for maintaining sterility. There are many designs to achieve this. In particular, the piercing member may be surrounded by a small piercing dome having an opening through which the piercing member extends. Such a piercing dome forms an open cavity that provides boundaries for the introduced sterile airflow in order to wrap the piercing member. The piercing dome is connected via an airflow tube to an air blower that is providing sterile air that has been produced by sterile filtering.

More preferably, the airflow device is providing a laminar flow of sterile air enveloping the piercing member of the injection device. Laminar airflows avoid turbulences that again increase the risk of introducing contaminated dust or droplets to the piercing member.

Preferably, the system comprises an air-filter system to reduce air contamination as described above. Additionally or alternatively, the system includes a disinfectant-spraying device adapted to spray disinfectant onto the piercing member. In this scenario even a microbial contamination of the piercing member that has already taken place is eliminated afterwards.

In a preferred embodiment, the injection device is held under a dome-like structure having a dome opening, the dome opening is facing the piercing member of the injection device. Such a dome-like structure offers the advantage of providing structural support for various devices of the intraocular injection system.

More preferably, the robotic manipulator is attached under the dome-like structure. Still the dome-like structure is preferably made of an optically transparent material. Thereby, patients, nurses and/or medical doctors are provided with increased structural oversight of the overall intraocular injection situation.

Preferably, the detection device comprises at least one camera attached to the dome-like structure. This camera serves in particular for visual control of the eye globe and/or the injector's movement. Furthermore, the camera may be used to scan the eye globe for the detection of the patch on the eye globe. The detection device may provide additional sensors, e.g., an ultrasound distance sensor. Preferably, such a distance sensor is arranged on the injection device to determine the distance between the needle's tip and the patch on the eye's globe. The camera can be arranged on the interior surface of the dome-like structure as well.

Preferably, a display device is attached to the dome-like structure. For example, the display device is formed by a plurality of LEDs and/or a monitor. The display device is adapted to attract the patient's attention in order to fix the patient's eyes globe prior and during the intraocular injection. This can be achieved by asking the patient to focus the eye globe onto displayed patterns or specific illuminated LEDs. More preferably, the system further comprises an acoustic communication device adapted for communication with the patient. The acoustic communication device comprises a microphone and/or a loudspeaker. If necessary, the patient can speak to medical staff such as a medical doctor or a nurse and/or can hear instructions given by the medical staff without the need for medical staff to be in the room where the injection is to be performed. Thereby, the system allows external audio communication. The acoustic communication device may be used in combination with the display device to display the medical staff while they are speaking and listening to the patient.

In a preferred embodiment, the dome-like structure is attached to a supporting arm device that is attachable to a supporting structure comprising any one or more of: a wall, a ceiling, a chair, a stand and a table. In a simple embodiment such a supporting structure is mechanically adjustable to move the intraocular injection system close to the eye ball of a patient. More preferably, the supporting arm device is configured and adapted for a manual movement of the dome-like structure in three dimensions. This provides more flexibility with regards to operability of the intraocular injection system. Even more preferred is that the supporting arm device further comprises a motorized positioning device providing at least three translational degrees of freedom for the movement of the dome-like structure.

As an alternative, full robotic movement functions are provided to the supporting arm device including a rotation of the dome providing the freedom to arrange all devices attached to the dome in a preferable position with respect to the patient.

In a preferred embodiment the detection device is provided with a camera such that the camera provides live imaging for a remotely-steered injection procedure. Thereby, the system allows visual remote communication. Thus, medical staff can control from afar the position of the injection device in relation to the patient's eye, preferably in combination with audio communication devices.

Preferably, the injection device is adapted to measure the force being required for an injection of the piercing member into the eye globe. This can be achieved by adding adapted force sensors to the injection device. Thereby, the intraocular injection process may be used to obtain important physiological data of the specific patient.

In a preferred embodiment the injection device comprises a sensor to measure intraocular pressure. The sensor can be adapted to measure intraocular pressure directly or indirectly by measuring a parameter by which the intraocular pressure can be calculated or at least estimated. The intraocular pressure is measured, for instance, by tonometry methods which are known in the art. For example air-tonometry, also called non-contact tonometry, wherein an air jet is used to applanate the cornea. The corneal applanation can be detected via an electro-optical system and the intraocular pressure can be calculated by using the mechanical force that is exerted by the air jet being used to provide the cornea applanation.

In a preferred embodiment, the injection device comprises a substance depot and a pump to deliver the substance to the piercing member. Alternatively, the injection device is adapted to use prefilled single-use syringes, drug containing vials as drug depots or long lasting depot drugs, e.g. Ozurdex. Thus, the system can be adapted to various piercing members such as needles, differing in length, width, and/or substances being used. Preferably, a standard needle for use with the injection system has a length of about 4 mm.

More preferably, the piercing member is an exchangeable single-use piercing member such as a needle. In a preferred embodiment the system comprises a single-use substance depot with a piercing member, wherein the injection process is provided electro-mechanically. The use of readily available, single-use syringes is also possible. However due to the length of the syringes' plunger, the resulting injection device would be lengthy.

In a preferred embodiment, the injection device includes a mechanical spring member configured and adapted to bias against an injection movement of the piercing member. Thereby, in the event of a power outage, the piercing member would be removed automatically by the mechanical spring member from the eye globe.

Preferably, the detection device is adapted to identify specific patients by iris recognition. Thus, treatment of a person other than the scheduled specific patient can be avoided. Furthermore, the injection system can comprise or be connected to a computer or database which provides data of specific patients. For example, the computer or database can contain stored patient information such as dates and/or substance amounts of last injections, number of injections made, drugs applied, allergies, injection point(s) of last injections and specific ocular measures. Upon the detection device identifying a specific patient, an associated controlling unit can control the injection device, e.g., can adapt the substance dose or change the substance depot, etc.

In a preferred embodiment, the robotic manipulator comprises a worm drive adapted and configured to provide a first rotational degree of freedom for the injection device. The worm drive includes a motorized worm screw and a worm gear in the form of a curved-gear rack that is being attached to the inner surface of the dome-like structure. The curvature of the gear rack may follow the curvature of the dome-like structure; however if more space is needed to arrange, for example, different sensors and cameras of the detection device, a different curvature providing more space may be used. Along the gear rack, the worm screw moves a slide and to this slide the injection device is attached.

More preferably, the robotic manipulator comprises a further worm drive attached to the first worm drive such that it provides a further rotational degree of freedom to the injection device having a rotational axis being oriented orthogonally to the first rotational degree of freedom. In order to obtain this combination of two rotational axes being oriented orthogonally to each other, a slide of the further worm drive is attached to the slide of the first worm drive. The further worm drive shows a further gear rack that is run through the further slide by the movement of the further worm drive's worm wheel. The injection device is attached to the gear rack of the further worm wheel thus providing two rotational axes controlled by two worm drives to the injection device.

The detection device or parts of it can be attached to the robotic manipulator and/or the injection device. When the injection system comprises a dome-like structure, the robotic manipulator and/or the detection device or parts of it are attached directly or indirectly to the dome-like structure.

22 Furthermore, the invention relates to a method for controlling an intraocular injection system, the method comprising the following steps:

providing one of the intraocular injection systems according to one or more of the embodiments described above, positioning the injection device coarsely above the eye globe, attaching a patch (P) to the eye globe (E) over an intraocular injection point, detecting a position of the patch on the eye globe by the detection device, removing a cover of the piercing member of the injection device, fine positioning the piercing member of the injection device above the detected patch based on the detected position of the patch.

The system identifies an injection point, the injection point is marked (e.g. by a visible laser device) and a nurse or an adapted patch-sticking device of the injection system attaches a patch to the eye globe's conjunctiva. In one preferred embodiment the eye globe's topology is detected before a patch is attached to the eye, in order to obtain a reference topology that can be compared to the topology detected after the patch has been attached. Thereby, the position of the patch is easily determined on the eye globe. Based on the determined position of the eye globe the injection device with its piercing member is moved to a pre-injection position after the cover of the piercing member has been removed.

The detection of the patch position is preferably done by topology analysis. For example a visible or infrared structured light pattern is projected onto the eye globe by a projection unit of the detection device and then the pattern is analyzed by the adapted camera(s) of the detection device to generate a three-dimensional surface map of the eye globe and its surroundings.

In a preferred embodiment, the method further comprises the step of starting an airflow of sterile air enveloping the piercing member of the injection device before removing the cover of the piercing member. This step provides a reliable sterile environment to the sterile piercing member prior and during injection. Instead of providing sterile conditions all around the patient's head it is sufficient to focus on the decisive area around the injection point and the piercing member. By this, compared to working under operating theater conditions a very cost and energy efficient system is provided.

Preferably, the method further comprises the step of using the detection device for tracking movement of the eye globe during the step of fine positioning of the injection device by moving the robotic manipulator. This step serves as a control feedback if the eye globe performs an undesirable movement. The compensatory movement in reaction to the detected eye globe movement may is done by the actuators of the robotic manipulator and/or the injection device.

In a preferred embodiment, the method further comprises the steps of piercing the piercing member through the patch into the eye globe and delivering the substance. After delivery of the substance, the piercing member is preferably retracted from the eye. Preferably, the penetration of the eye globe is done to perform an injection of a substance into the eye globe. However, as an alternative or in combination it is as well possible to extract tissue and/or liquid from the inside of the eye globe via the piercing member or to place and use other instruments inside the eye globe if the piercing member is a trocar.

Preferably, the method further comprises the step of using the detection device for tracking movement of the eye globe during the step of piercing the piercing member through the patch into the eye globe and during the step of delivering the substance, in order to maintain a relative position of the piercing member to the eye globe. The eye tracking may be used as part of a feedback control process. The compensatory movement to maintain the relative position of the piercing member to the eye globe is performed by the various actuators of the robotic manipulator and/or the injection device.

In the following figures one exemplary embodiment of the invention is shown together with some variations.

DETAILED DESCRIPTION

Figure 1:
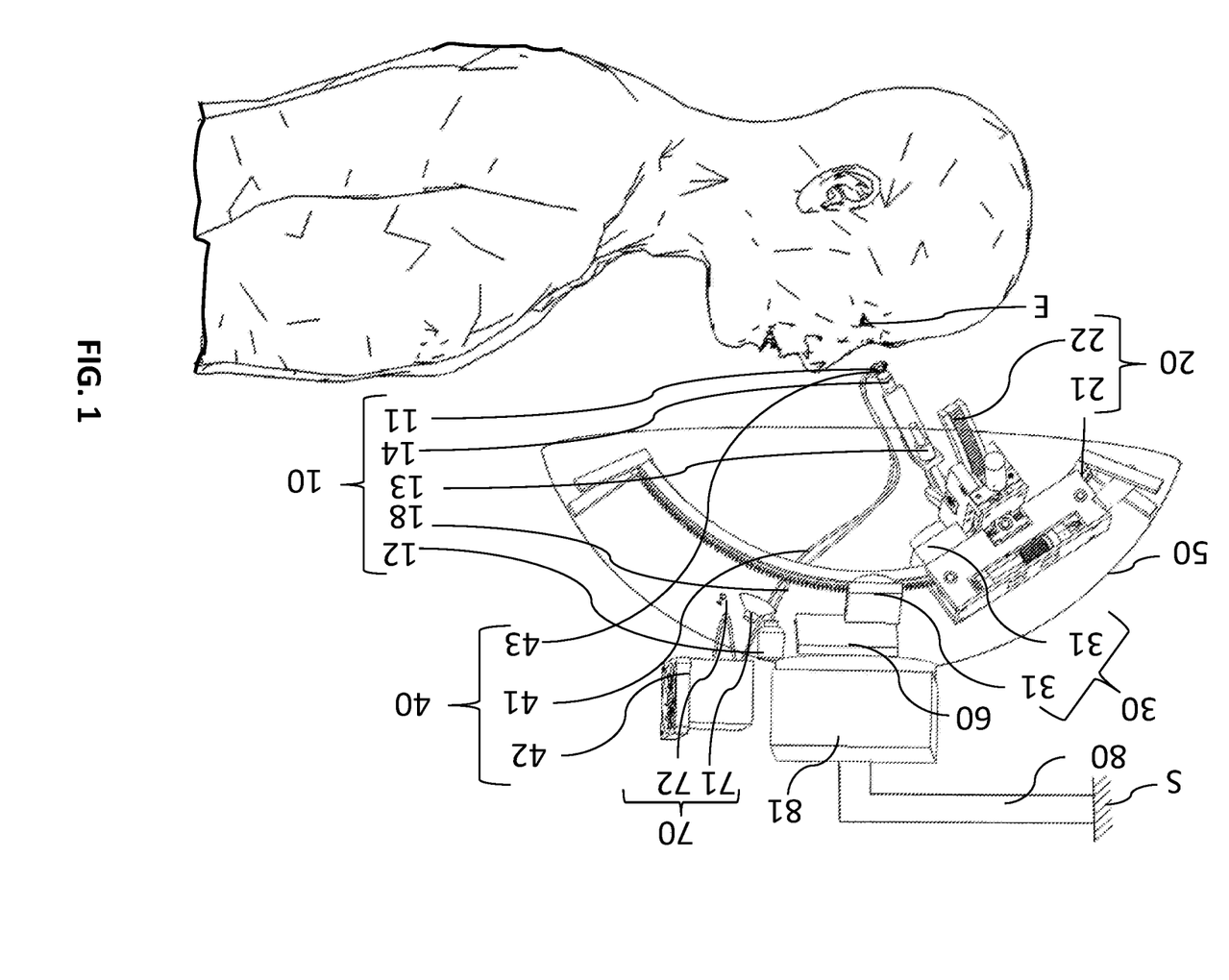
FIG. 1 shows a schematic side view of an intraocular injection system according to one exemplary embodiment of the invention, together with an upper body part of a patient.

FIG. 1 shows a schematic side view of an intraocular injection system according to one exemplary embodiment of the invention together with an upper body part of a patient. As basic functional groups, the intraocular injection system comprises the combination of an injection device 10, a robotic manipulator 20, and a detection device 30. All of these functional groups are installed directly or indirectly to the inside surface of a dome-like structure 50 made by an optically transparent material. Thereby, all of these devices can be moved above the head of a patient by moving the dome-like structure 50.

The injection device 10 comprises a piercing member 11 which can be inserted into an eye globe E of the patient shown following a linear path provided by a spindle-drive motor device 13. The piercing member 11 has the form of a needle and is connected to a syringe body 14. The syringe body 14 is connected to a pump (not shown) and a substance depot 12 via a substance tube 18. In use, a substance can be delivered from the substance depot 12 and by activating the pump via the substance tube 18 and the syringe body 14 to the piercing member 11. Furthermore, the spindle drive motor device 13 is moving the piercing member 11, together with the syringe body 14 on the linear path of the intraocular injection. As a substance pump the following system can be used, Curiejet® Liquid Micropump PS15I (Microj et Co. Ltd., Hsinchu, Taiwan). For the spindle drive motor device a Maxon A-max 16 motor is used together with a spindle gear GP16 of Maxon Motor AG, Sachseln, Switzerland.

The robotic manipulator 20 has a first worm drive 21 showing a slide that can run along curved gear rack that is also installed to the inside surface of the dome-like structure 50 following its inner curvature. Attached to the slide of the first worm drive 21 is the slide of a further worm drive 22 showing a further curved track gear that extends orthogonally to the track gear of the first worm drive 21. To the end portion of this further track gear the injection device 10 is attached. Thereby, the first worm drive 21 of the robotic manipulator 20 is adapted and configured to provide a first rotational degree of freedom for the injection device 10. The further worm drive 22 of the robotic manipulator 20 provides a further rotational degree of freedom to the injection device 10 having a rotational axis being oriented orthogonally to the first rotational degree of freedom. Those worm drives are, for example, driven by Maxon DCmax16S motors with a GPX165.3:1 gear and an ENX10EASY encoder produced by Maxon Motor AG, Sachseln, Switzerland.

According to a variation of the invention's embodiment the detection device 30 comprises two cameras 31. One camera is attached to the inner surface of the dome-like structure 50 and the other camera is attached to the slide of the first worm drive 21. As an alternative, one of the two cameras 31 could be replaced by a structured light emitting device cooperating with the other camera 31. One example for a camera that can be used for such a system is See3CAM_12CUNIR-1.3 MP from e-con Systems Pvt. Limited (St. Louis, USA/Chennai, India).

Furthermore, the depicted embodiment of the intraocular injection system comprises an airflow device 40 providing a flow of sterile air enveloping the piercing member 11 of the injection device 10. The airflow device 40 comprises a piercing dome 43 attached to the tip of the injection device 10 partially embracing the piercing member 11. Furthermore, the piercing dome 43 is connected by an airflow tube 41 to an air blower 42 that is providing sterile air, for example, by using appropriate air filters.

Furthermore, a display device 60 is attached to the dome-like structure 50 to optically attract the attention of the patient shown. The display device 60 also serves to establish optical communication between the patient and medical staff that is not present near the patient.

The intraocular injection system further comprises an acoustic communication device 70 attached to the dome-like structure 50. The acoustic communication device 70 is adapted for communicating with the patient shown and comprises a loudspeaker 71 and a microphone 72. In addition to the optical communication via the display device 60, the acoustic communication device 70 adds to the system the option of voice and sound communication between the patient and medical staff.

The dome-like structure 50 is attached to a supporting arm device 80 that is attached to a supporting structure S, for example, a wall. The supporting arm device 80 is configured and adapted for a manual movement of the dome-like structure 50 in three dimensions. These properties enable a coarse positioning of the dome-like structure above a patient's head. Furthermore, the supporting arm device 80 shows a motorized positioning device 81 providing at least three translational degrees of freedom for the movement of the dome-like structure 50. In addition to these three translational degrees of freedom a rotation of the dome-like structure 50 is advantageous as well. Together with the movement of the robotic manipulator 20, the motorized positioning device 81 provides fine positioning for moving the injection device 10 to a pre-injection position. As an example, the motorized positioning device 81 comprises a three-axis positioner combining two MTS50-Z8 and one MTS25-Z8 from Thorlabs, Inc., Newton, N.J., USA.

The different method steps for providing intraocular injections using this embodiment of the intraocular injection system will be explained below in relation to FIGS. 4a to 4d.

Figure 2:
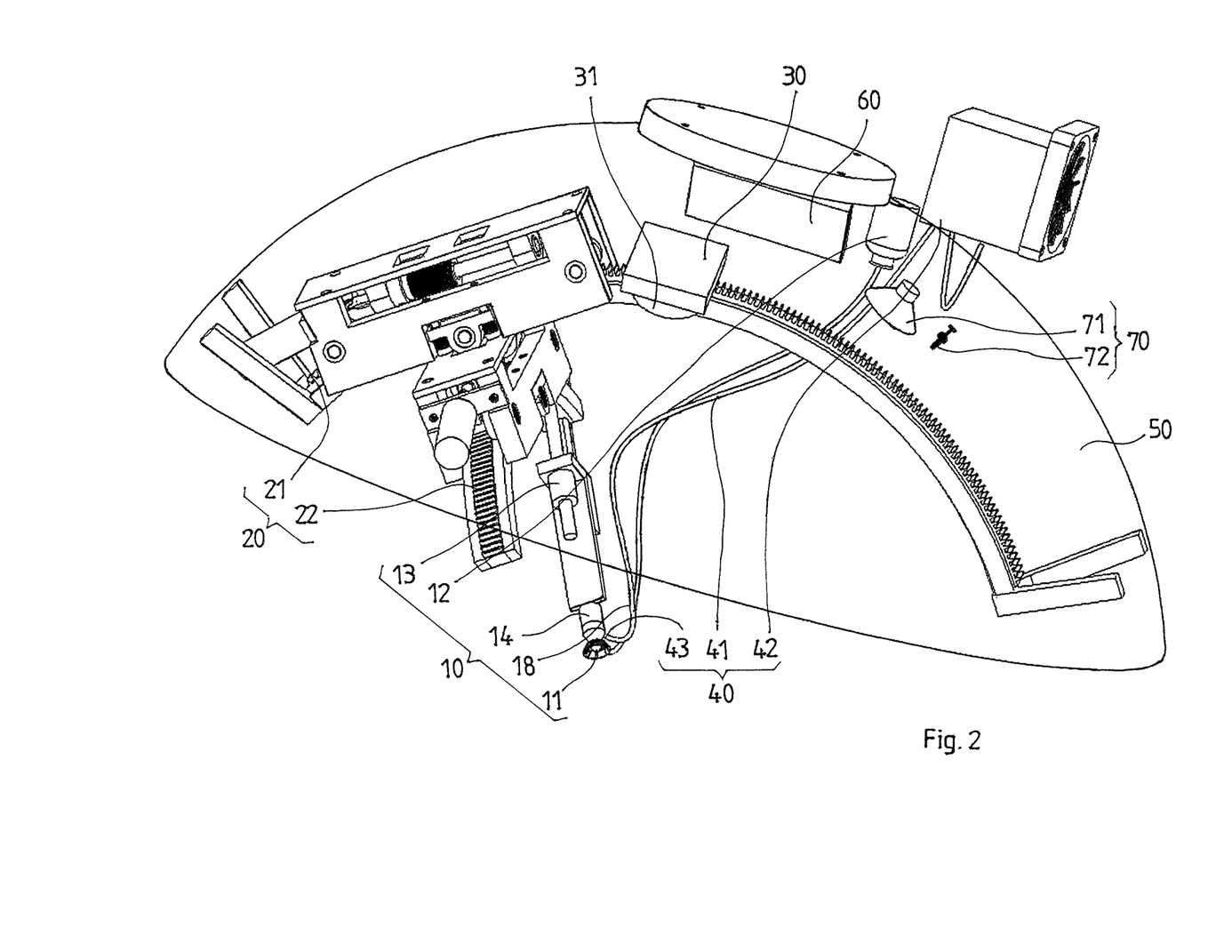
FIG. 2 shows a closer view of the embodiment of FIG. 1 with a small variation regarding the detection device 30.

FIG. 2 shows a closer view of the embodiment of FIG. 1 with a small variation regarding the detection device 30. Further parts of the system, like the supporting arm device 80, the supporting structure S and the motorized positioning device 81, are not shown for the sake of simplicity. With regards to injection device 10, robotic manipulator 20, airflow device 40, dome-like structure 50, display device 60, and acoustic communication device 70, this intraocular injection system corresponds exactly to FIG. 1. Therefore, a description of such elements will not be repeated with respect to this embodiment, as it will be understood that the structure and function of such elements is substantially the same as that described above. The only difference lies in the detection device 30. The detection device 30 of the injection system includes only one camera 31 that is attached to the inner surface of the dome-like structure 50. No second camera attached to the robotic manipulator 20 is provided. The detection device 30 of the injection system shown in FIG. 2 can further comprise a distance sensor (not shown) attached to the injection device 10.

Figure 3:
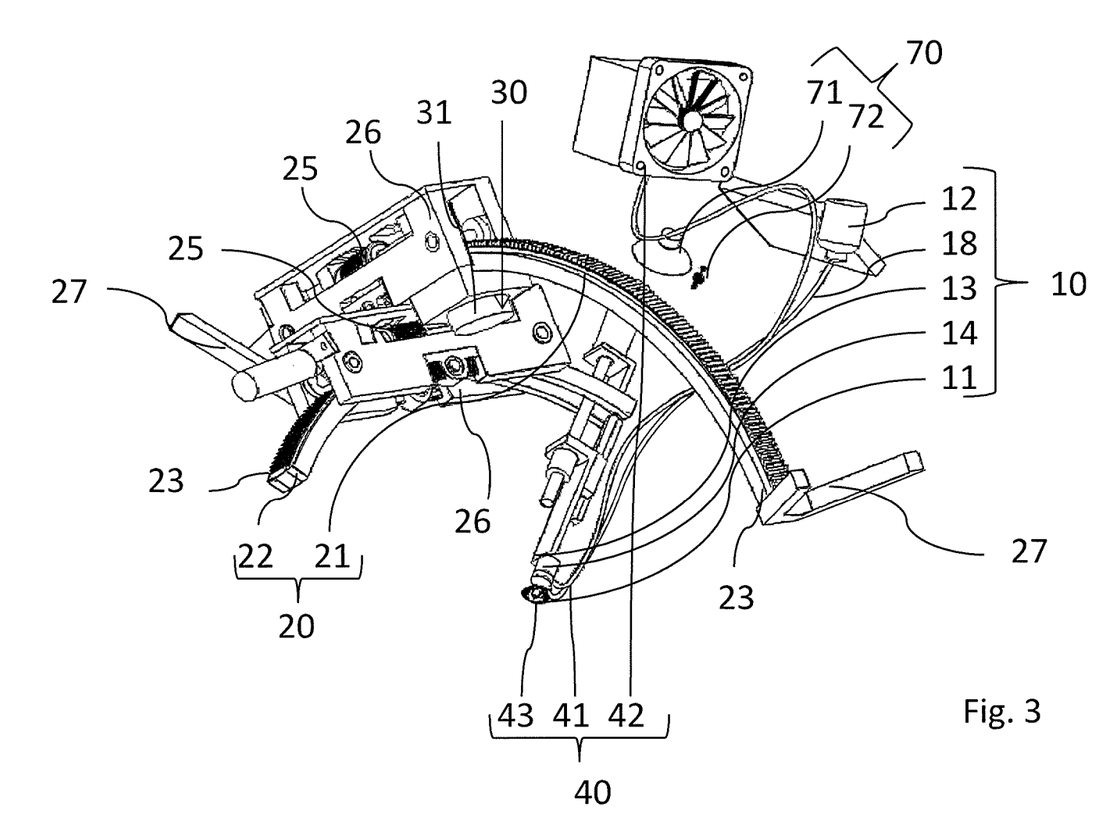
FIG. 3 shows the intraocular injection device of FIG. 2 from a slightly different angle with another small variation regarding the position of the detection device 30.

FIG. 3 shows the intraocular injection device of FIG. 2 from a slightly different angle with another small variation regarding the position of the detection device 30. The dome-like structure 50 shown in FIG. 2 is not shown for sake of simplicity. The first worm drive 21 and the further worm drive 22 each have a gear rack 23 having a curved shape. The gear rack 23 of the first worm drive 21 is attached to the inner surface of the dome-like structure 50 (not shown) by V-shaped attaching means 27 that are provided at both ends of the gear rack 23.

Each of the first and further worm drives 21, 22 has a motorized worm screw 25, which meshes with the respective gear track 23 to displace the injection device 10 into the desired position. Each motorized worm screw 25 of each worm drive is respectively arranged in a slide 26. Each of the slides 26 houses a motor to drive the worm screws 25 that are meshing with their respective gear racks 23, thereby displacing the slides 26 following the curved trajectory defined by the gear racks 23.

According to FIG. 3 a variation with respect of the detection device 30 is shown. Unlike in the previous variations, the only camera 31 of the detection device 30 is arranged on the slide 26 of the first worm drive 21.

FIGS. 4a to 4d schematically show a sequence of method steps for controlling an intraocular injection using the intraocular injection system shown in FIGS. 1 to 3. For sake of simplicity, only an eye globe E of a patient and the front section of the injection device 10 of the intravitreal injection system are shown in FIGS. 4a to 4d. The injection device 10 comprises a cylindrical syringe body 14 having a cavity. This cavity is divided by a membrane 15 into an upper cavity part and a lower cavity part. The lower cavity part shows a first opening having a first valve 16 and a second opening having a second valve 17. Via the first opening and its first valve 16, the lower cavity part is connected by a substance tube (not shown) to a liquid substance reservoir (not shown). The first valve 16 opens in the direction of the lower cavity part. Via the second opening and the second valve 17 the lower cavity part of the syringe body 14 is connected to a piercing member 11 in the form of an injection needle that is protected by a cover 19. The second valve 17 opens in the direction of the piercing member 11.

Figure 4A:
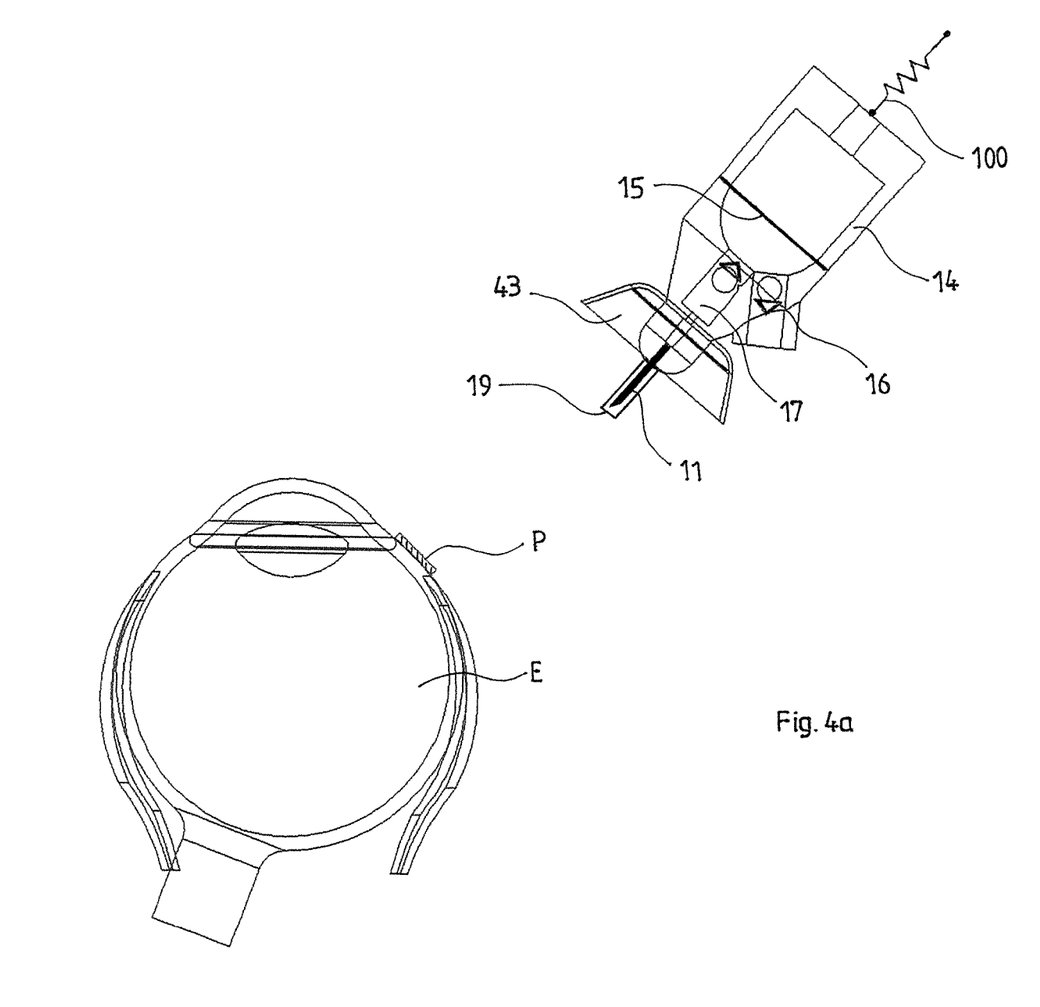
FIGS. 4a to 4d schematically show a method sequence for controlling an intraocular injection using the intraocular injection system.
Figure 4B:
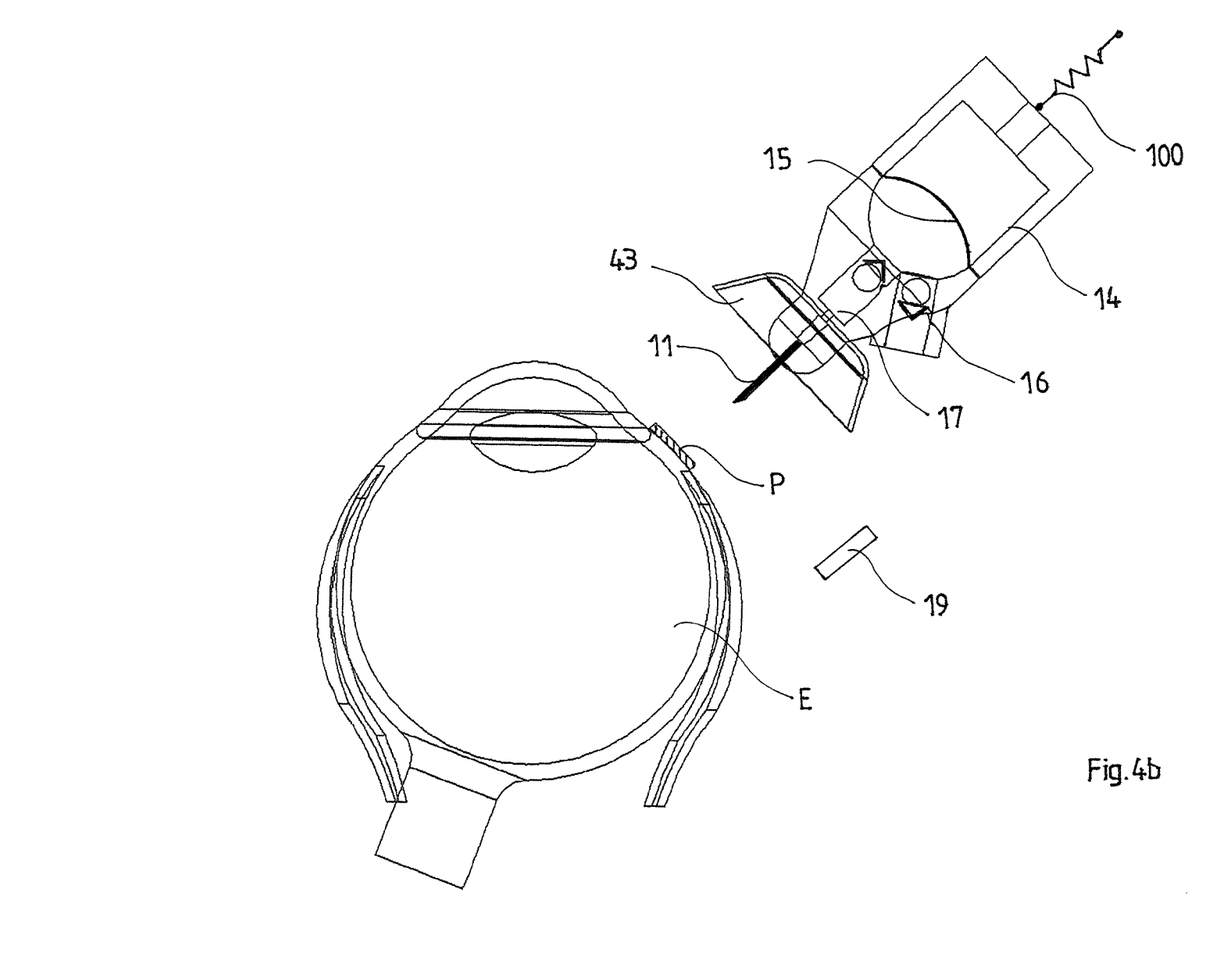

To prepare an injection into an eye globe, a patch P must firstly be stuck on top of the injection site to the conjunctiva. The patch P provides a disinfecting agent at least to the area of the conjunctiva that is covered by the patch. After that, the sterile airflow enveloping the piercing member 11 and escaping from the piercing dome 43 is activated, after that the cover 19 of the piercing member 11 is removed and the injection device 10 is translated to a pre-injection position as can be seen in FIG. 4b.

The upper cavity part shows an opening that is connected to a pump (not shown). If the pump creates a vacuum, the membrane 15 is deflected in the direction of the upper cavity part of the syringe body 14 as shown in FIG. 4b. Thereby, the liquid substance is pulled from the substance reservoir through the substance tube and the first valve 16 into the lower cavity part that is enlarged by the membrane deflection.

Figure 4C:
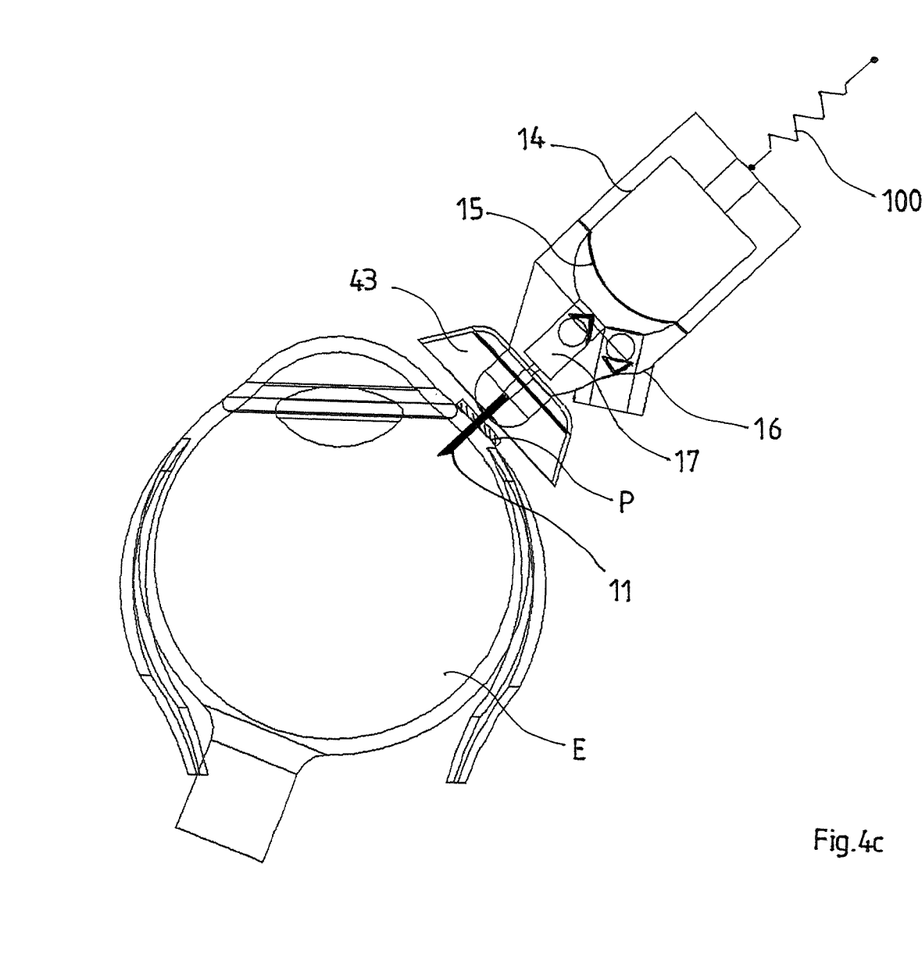

Now, the injection device 10 is ready for automatically performing an injection movement of the piercing member 11 into the eye globe E. As shown in FIG. 4c the piercing member 11 of the injection device 10 is pierced through the patch P into the eye globe E by an electric power-driven translational movement. This movement is biased against a mechanical spring member 100. If a power outage were to occur, the biased mechanical spring member 100 would retract the piercing member 11 from the eye globe E.

The pump provides pressure to the upper cavity of the syringe body 14. Thereby, the membrane is deflected into the direction of the lower cavity part. Consequently, the first valve 16 is forced into its closed position and the second valve 17 is forced into its open position allowing the liquid substance to press through this valve and through the piercing member 11 into the eye globe E.

Figure 4D:
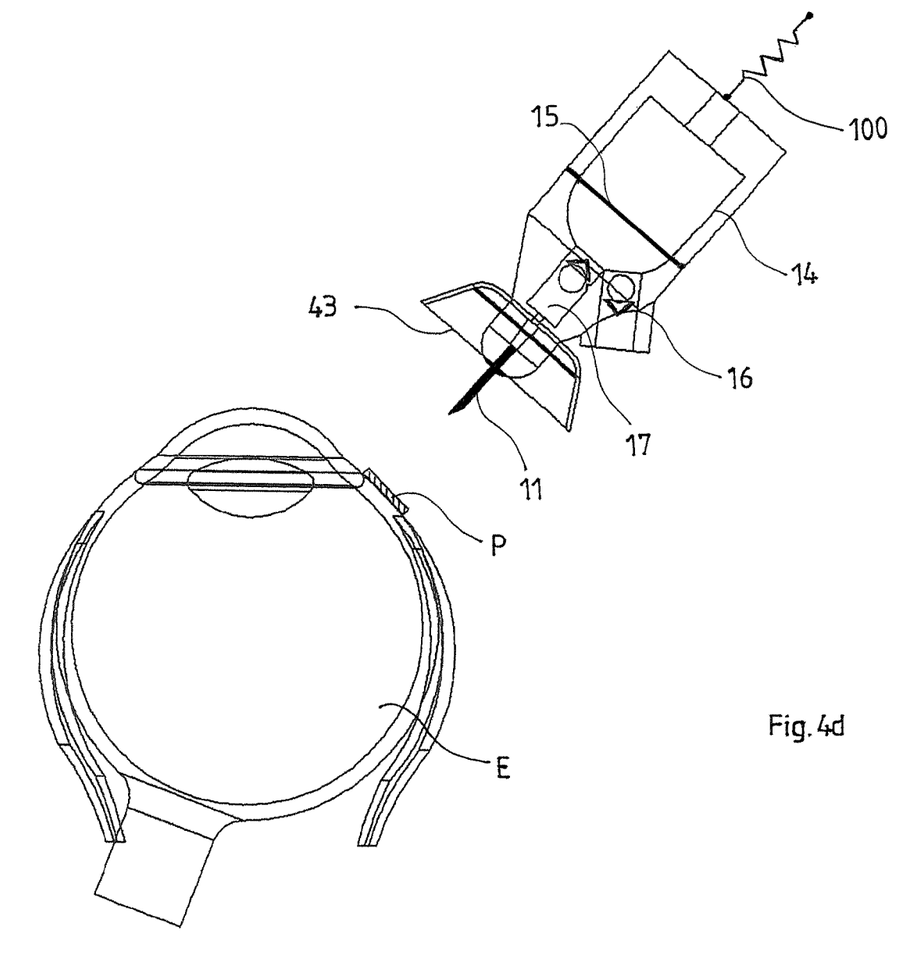

Finally, the piercing member 11 is removed from the eye globe E and held in an after-injection position, as shown in FIG. 4*d*.

LIST OF REFERENCE NUMBERS

10 injection device
11 piercing member
12 substance depot
13 spindle motor device
14 syringe body
15 membrane
16 first valve
17 second valve
18 substance tube
19 cover
100 mechanical spring member
20 robotic manipulator
21 first worm drive
22 further worm drive
23 gear rack
25 motorized worm screw
26 slide
27 attaching means
30 detection device
31 camera
32 distance sensor
40 airflow device
41 airflow tube
42 air blower
43 piercing dome
50 dome-like structure
60 display device
70 acoustic communication device
71 loudspeaker
72 microphone
80 supporting arm device
81 motorized positioning device
E eye globe
P patch
S supporting structure

The invention claimed is:

1. An intraocular injection system for injecting a substance into an eye globe of an animal or human eye, the system comprising:
   an injection device with a piercing member for injection of the substance into the eye globe, the intraocular injection system providing an automated piercing of the eye globe by the piercing member,
   a robotic manipulator carrying the injection device, the robotic manipulator adapted and configured to move the injection device to a pre-injection position, and
   a detection device adapted and configured to detect a position of a patch placed onto the eye globe and to control the robotic manipulator to move the injection device to the pre-injection position, the pre-injection position being based upon the detected position of the patch on the eye globe.

2. The intraocular injection system according to claim 1, wherein the detection device is adapted and configured to detect a difference between a topology of the eye globe without the patch and a resultant topology of the combined eye globe and patch.

3. The intraocular injection system according to claim 1, wherein the system further comprises an airflow device providing a flow of sterile air enveloping the piercing member of the injection device.

4. The intraocular injection system according to claim 3, wherein the airflow device is providing a laminar flow of sterile air enveloping the piercing member of the injection device.

5. The intraocular injection system according to claim 1, wherein the injection device is held under a dome-like structure having a dome opening, the dome opening is facing the piercing member of the injection device.

6. The intraocular injection system according to claim 5, wherein the robotic manipulator is attached under the dome-like structure.

7. The intraocular injection system according to claim 5, wherein the detection device comprises at least one camera being attached to the dome-like structure.

8. The intraocular injection system according to claim 5, wherein a display device is attached to the dome-like structure.

9. The intraocular injection system according to claim 8, wherein the system further comprises an acoustic communication device for communication with a patient.

10. The intraocular injection system according to claim 5, wherein the dome-like structure is attached to a supporting arm device that is attachable to a supporting structure comprising any one or more of a wall, a ceiling, a chair, a stand and a table.

11. The intraocular injection system according to claim 10, wherein the supporting arm device is configured and adapted for a manual movement of the dome-like structure in three dimensions.

12. The intraocular injection system according to claim 11, wherein the supporting arm device further comprises a motorized positioning device providing at least three translational degrees of freedom for the movement of the dome-like structure.

13. The intraocular injection system according to claim 1, wherein the detection device is provided with a camera such that the camera provides live imaging for a remotely-steered injection procedure.

14. The intraocular injection system according to claim 1, wherein the injection device is adapted to measure a force being required for an injection of the piercing member into the eye globe.

15. The intraocular injection system according to claim 1, wherein the injection device comprises a substance depot and a pump to deliver the substance to the piercing member.

16. The intraocular injection system according to claim 15, wherein the piercing member is an exchangeable single-use piercing member.

17. The intraocular injection system according to claim 1, wherein the injection device includes a mechanical spring member configured and adapted to bias against an injection movement of the piercing member.

18. The intraocular injection system according to claim 1, wherein the detection device is adapted to identify specific patients by iris recognition.

19. The intraocular injection system according to claim 1, wherein the robotic manipulator comprises a first worm drive adapted and configured to provide a first rotational degree of freedom for the injection device.

20. The intraocular injection system according to claim 19, wherein the robotic manipulator comprises a further worm drive attached to the first worm drive such that the further worm drive provides a further rotational degree of freedom to the injection device, the further worm drive having a rotational axis being oriented orthogonally to the first rotational degree of freedom.

21. A method for controlling an intraocular injection system, the method comprising the following steps:
   providing the intraocular injection system according to claim 1,
   positioning the injection device above the eye globe,
   attaching the patch to the eye globe over an intraocular injection point,
   detecting the position of the patch on the eye globe by the detection device,
   removing a cover of the piercing member of the injection device,
   positioning the piercing member of the injection device above the detected patch based on the detected position of the patch.

22. The method according to claim 21, further comprising a step of starting an airflow of sterile air enveloping the piercing member of the injection device before removing the cover of the piercing member.

23. The method according to claim 21, further comprising a step of using the detection device for tracking movement of the eye globe during the step of positioning the piercing member of the injection device by moving the robotic manipulator.

24. The method according to claim 21, further comprising a step of piercing the piercing member through the patch into the eye globe and a step of delivering the sub stance.

25. The method according to claim 24, further comprising a step of using the detection device for tracking movement of the eye globe during the step of piercing the piercing member through the patch into the eye globe and during the step of delivering the substance, in order to adapt a relative position of the piercing member to the eye globe.

* * * * *